United States Patent
Matsumoto et al.

(10) Patent No.: US 9,032,813 B2
(45) Date of Patent: May 19, 2015

(54) TORSION TESTER

(71) Applicant: KOKUSAI KEISOKUKI KABUSHIKI KAISHA, Tokyo (JP)

(72) Inventors: Sigeru Matsumoto, Tokyo (JP); Hiroshi Miyashita, Tokyo (JP); Kazuhiro Murauchi, Tokyo (JP); Masanobu Hasegawa, Tokyo (JP); Tomotaka Sakagami, Tokyo (JP); Yasuyuki Mido, Aichi (JP); Shigenobu Kawai, Aichi (JP)

(73) Assignee: KOKUSAI KEISOKUKI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/228,862

(22) Filed: Mar. 28, 2014

(65) Prior Publication Data
US 2014/0208864 A1  Jul. 31, 2014

Related U.S. Application Data

(63) Continuation-in-part of application No. PCT/JP2012/074635, filed on Sep. 26, 2012.

(30) Foreign Application Priority Data

Sep. 30, 2011 (JP) ................. 2011-218790

(51) Int. Cl.
*G01N 3/22* (2006.01)
*G01N 3/08* (2006.01)

(52) U.S. Cl.
CPC ... *G01N 3/08* (2013.01); *G01N 3/22* (2013.01)

(58) Field of Classification Search
CPC ................. G01L 5/0042; G01M 13/02
USPC ................. 73/862.325, 847, 862.324
See application file for complete search history.

(56) References Cited

U.S. PATENT DOCUMENTS

| | | | | |
|---|---|---|---|---|
| 4,354,144 A | * | 10/1982 | McCarthy | 318/13 |
| 4,712,052 A | * | 12/1987 | Omae et al. | 318/625 |
| 4,989,686 A | * | 2/1991 | Miller et al. | 180/197 |

(Continued)

FOREIGN PATENT DOCUMENTS

| | | |
|---|---|---|
| JP | 03-200043 | 9/1991 |
| JP | 2000-193574 | 7/2000 |

(Continued)

OTHER PUBLICATIONS

International Search Report issued in PCT/JP2012/074635.
(Continued)

*Primary Examiner* — Max Noori
(74) *Attorney, Agent, or Firm* — McCarter & English, LLP

(57) ABSTRACT

A torsion tester including a reaction force unit and a drive unit including a servo motor, a first reduction gear, a shaft transmitting an output force from the first reduction gear, a clutch having an input shaft fixed to the shaft, a second reduction gear decelerating rotation of an output shaft of the clutch, a chuck, and a connection mechanism connecting the chuck with one of the shaft and the second reduction gear, the drive unit configured to switch between a first mode where the clutch is disengaged, and the shaft is connected with the chuck by the connection mechanism and a second mode where the clutch is engaged, and the second reduction gear is connected with the chuck by the connection mechanism.

9 Claims, 6 Drawing Sheets

(56) References Cited

U.S. PATENT DOCUMENTS 5,741,200 A * 4/1998 Taniguchi et al. .............. 477/93
2006/0017414 A1 * 1/2006 Joe et al. ....................... 318/432

FOREIGN PATENT DOCUMENTS

| | | |
|---|---|---|
| JP | 2004-125549 | 4/2004 |
| JP | 2006-064668 | 3/2006 |
| JP | 2007-107955 | 4/2007 |
| JP | 2008-267939 | 11/2008 |

OTHER PUBLICATIONS

International Preliminary Report on Patentability issued in Application No. PCT/JP2012/074635 on Apr. 10, 2014.

* cited by examiner

TORSION TESTER

CROSS-REFERENCE TO RELATED APPLICATION

This is a Continuation-in-Part of International Application No. PCT/JP2012/074635 filed on Sep. 26, 2012, which claims priority from Japanese Patent Application No. 2011-218790 filed on Sep. 30, 2011. The entire disclosure of the prior applications is incorporated herein by reference.

BACKGROUND

1. Technical Field

The following description relates to one or more techniques for a torsion tester, particularly, for a torsion tester configured to conduct both a fatigue test to repeatedly apply to a test body a load in a regularly-used load range over a long period of time and a destructive test to apply to the test body a great load in a breaking load range.

2. Related Art

So far, in order to conduct a fatigue test (a torsion test) for a power transmission component such as a propeller shaft, a hydraulic tester has mostly been used that is configured to generate a repeated load varying at a high frequency. However, in order to attain a great torque and a great displacement required for driving the test body in a destructive test (a torsional destructive test) using the hydraulic tester, a huge hydraulic system needs to be provided. Hence, an electric-motor-type tester is mostly used in the destructive test.

Additionally, in recent years, a low-inertia-type servo motor has been put to practical use that is configured to generate a torque varying at a high frequency, and a servo-motor-type fatigue tester is beginning to be used.

SUMMARY

However, between the fatigue test and the destructive test, there are differences in the required torque and the required frequency of torque variation. Thus, it has been impossible to conduct both the fatigue test and the destructive test with a single tester.

Aspects of the present invention are advantageous to present one or more improved techniques, for a torsion tester, which make it possible to resolve the aforementioned problem.

According to aspects of the present invention, a torsion tester is provided, which includes a reaction force unit configured to clamp one end of a test body, and a drive unit configured to rotatably support and drive another end of the test body, the drive unit including a servo motor, a first reduction gear configured to decelerate rotation of the servo motor at a first reduction ratio, a shaft configured to transmit an output force from the first reduction gear, a clutch having an input shaft fixed to the shaft, a second reduction gear configured to decelerate rotation of an output shaft of the clutch at a second reduction ratio, a chuck rotatably supported, and a connection mechanism configured to connect the chuck switchably with one of the shaft and an output shaft of the second reduction gear, the drive unit configured to switch between a first mode where the clutch is disengaged to interrupt power transmission between the input shaft of the clutch and the output shaft of the clutch, and the shaft is connected with the chuck by the connection mechanism, and a second mode where the clutch is engaged to establish the power transmission between the input shaft of the clutch and the output shaft of the clutch, and the output shaft of the second reduction gear is connected with the chuck by the connection mechanism.

According to aspects of the present invention, further provided is a torsion tester that includes a reaction force unit configured to clamp one end of a test body, and a drive unit configured to rotatably support and drive another end of the test body, the drive unit including a servo motor, a first reduction gear configured to decelerate rotation of the servo motor at a first reduction ratio, a shaft configured to transmit an output force from the first reduction gear, a clutch including an input shaft fixed to the shaft and configured to be driven by the rotation decelerated by the first reduction gear via the shaft, an output shaft and a joint mechanism engaged with the output shaft of the clutch, the joint mechanism configured to switch between a first-mode state where the joint mechanism is disengaged from the input shaft of the clutch and a second-mode state where the joint mechanism is engaged with the input shaft of the clutch, a second reduction gear configured to decelerate rotation of the output shaft of the clutch at a second reduction ratio, a chuck configured to connect switchably with one of the shaft and an output shaft of the second reduction gear, and is driven by rotation of the one of the shaft and the output shaft of the second reduction gear, the drive unit configured to switch between a first mode where the joint mechanism is set in the first-mode state such that the clutch is disengaged to interrupt power transmission between the input shaft of the clutch and the output shaft of the clutch, and the chuck is connected with the shaft without involving the second reduction gear, and a second mode where the joint mechanism is set in the second-mode state such that the clutch is engaged to establish the power transmission between the input shaft of the clutch and the output shaft of the clutch via the joint mechanism, and the chuck is connected with the output shaft of the second reduction gear.

BRIEF DESCRIPTION OF THE ACCOMPANYING DRAWINGS

DETAILED DESCRIPTION

It is noted that various connections are set forth between elements in the following description. It is noted that these connections in general and, unless specified otherwise, may be direct or indirect and that this specification is not intended to be limiting in this respect.

Figure 1:
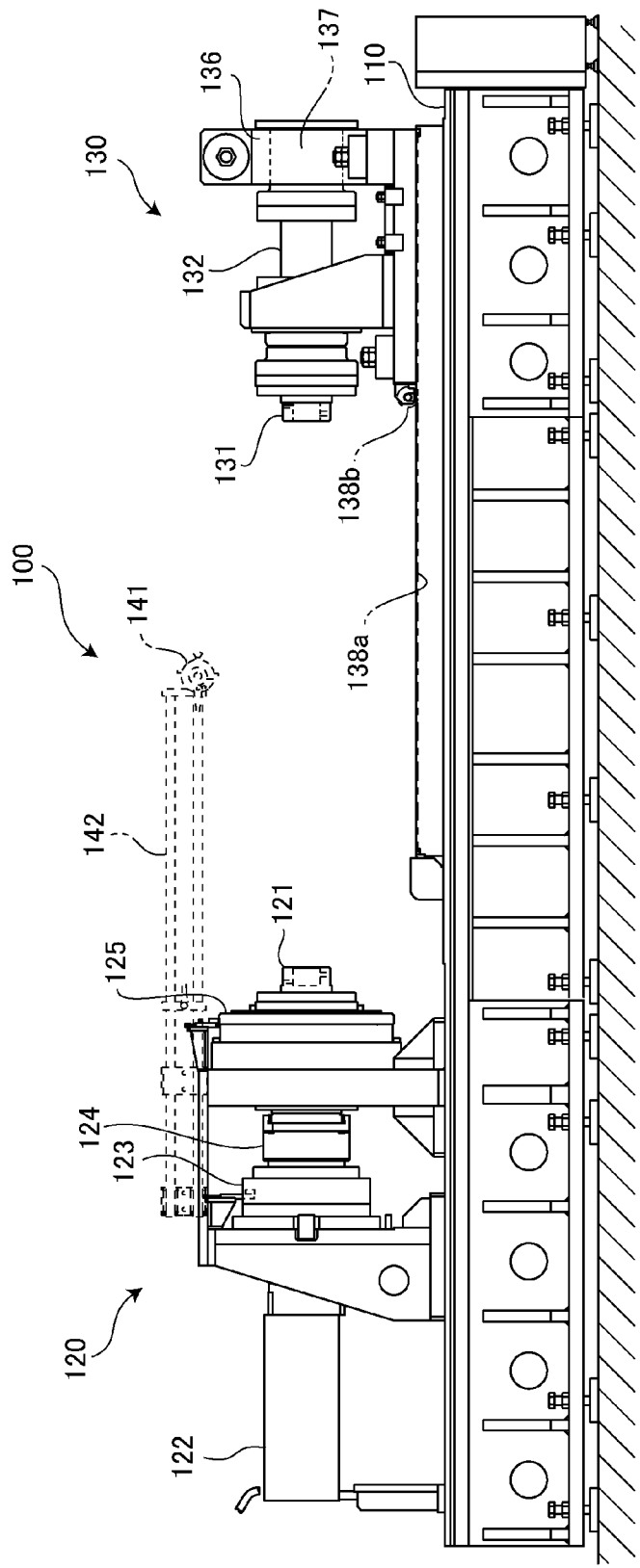
FIG. 1 is a side view of a torsion tester in an embodiment according to one or more aspects of the present invention.

Hereafter, an embodiment according to the present invention will be described with reference to the accompanying drawings. FIG. 1 is a side view of a torsion tester 100 in an embodiment of the present invention. As shown in FIG. 1, the torsion tester 100 of the embodiment is configured such that a drive unit 120 and a reaction force unit 130 are disposed on a base 110. Chucks 121 and 131 are provided to the drive unit 120 and the reaction force unit 130, respectively. When a test body is clamped by the chucks 121 and 131, and the chuck 121 is driven to rotate by the drive unit 120, it is possible to apply a torsional load to the test body. The reaction force unit 130 is configured to serve as a fixed end of the test body, and measure a torque applied to the test body with a torque sensor 132 provided to the reaction force unit 130.

The drive unit 120 includes a servo motor 122, a first reduction gear 123, a clutch 124, and a second reduction gear 125. The drive unit 120 of the embodiment is configured to, when the clutch 124 is operated, change a reduction ratio of the chuck 121 to the servo motor 122. Specifically, the drive unit 120 is configured to switch between a first mode in which a rotational shaft of the servo motor 122 is connected only with the first reduction gear 123 so as to achieve a small reduction ratio, and a second mode in which the rotational shaft of the servo motor 122 is connected in series with the first reduction gear 123 and the second reduction gear 125 so as to achieve a large reduction ratio. The first mode can be employed in an endurance test (e.g., a fatigue test) in which a load is applied to the test body repeatedly at a high frequency. The second mode can he employed in a destructive test (a torsional destructive test) in which a great torque (equal to or more than a breaking torsional load) is applied to the test body.

Figure 2:
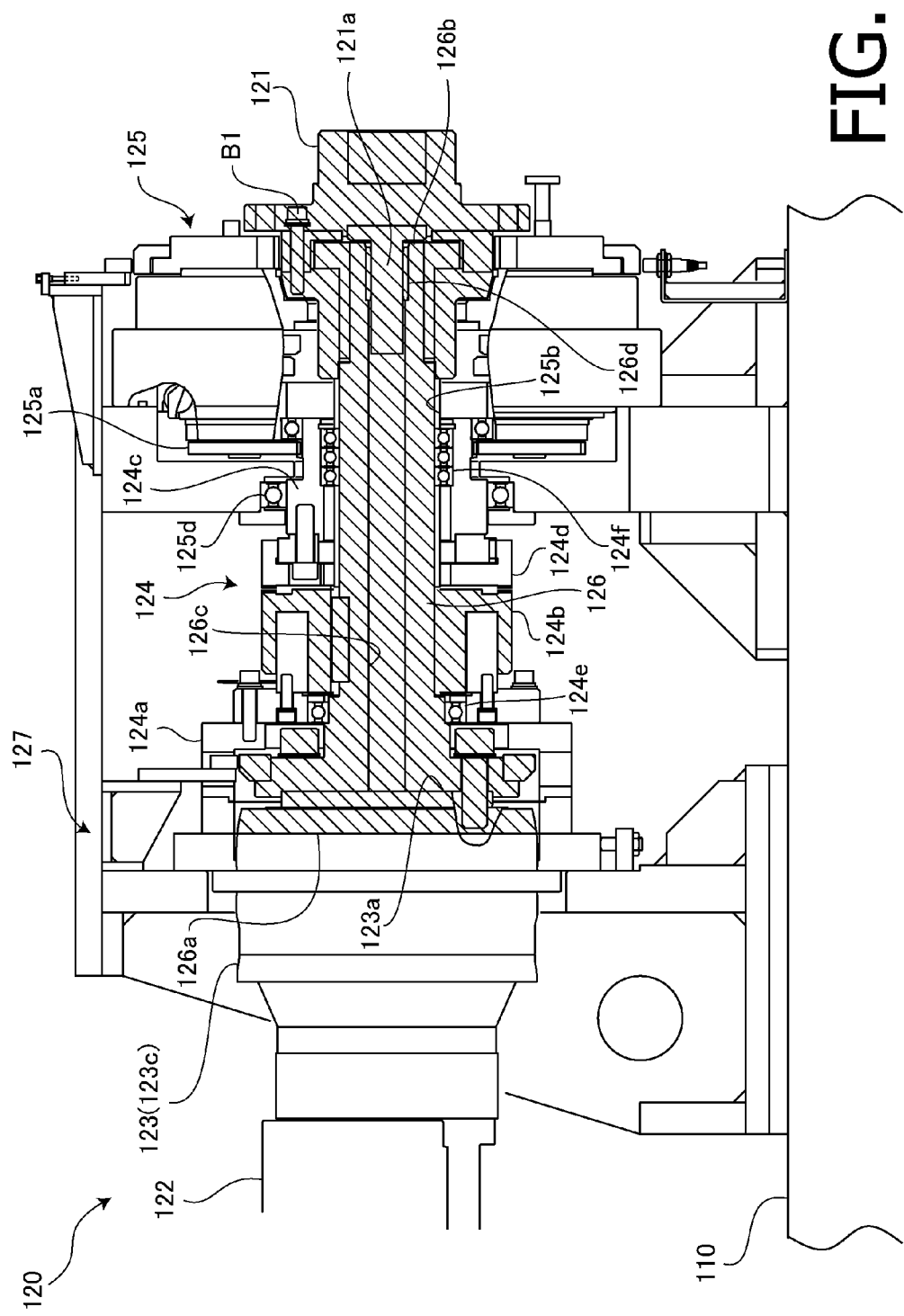
FIG. 2 is a cross-sectional side view showing a drive unit of the torsion tester in a first mode in the embodiment according to one or more aspects of the present invention.

Hereinafter, an explanation will be provided about a mechanism for switching between the first mode and the second mode. FIG. 2 is a cross-sectional side view showing the drive unit 120 in the first mode.

An output shaft (not shown) of the servo motor 122 is fixed to an input shaft (not shown) of the first reduction gear 123. Further, an input end 126a of a shaft 126 is fixed to an output end 123a of the first reduction gear 123. Rotation of the output shaft of the servo motor 122 is decelerated by the first reduction gear 123 and transmitted to the shaft 126. The shaft 126 has a through hole 126c formed to extend on and along a center axis (a rotation axis) of the shaft 126. Thus, the shaft 126 is configured to ensure a high torsional rigidity with a large outside diameter, and achieve a low inertia, so as to be driven to reversely rotate at a high frequency. It is noted that the shaft 126 extends along the rotation axis from the output end 123a of the first reduction gear 123 through (hollow portions provided in) the clutch 124 and the second reduction gear 125. In addition, a case 123c of the first reduction gear 123 is fixed to a driver-side frame 127, which forms a high-stiffness device frame together with the base 110.

The clutch 124 includes a fixed portion 124a, an input shall 124b, an output shaft 124c, and a movable joint shaft 124d. The fixed portion 124a is fixed to and supported by driver-side frame 127. Each of the fixed portion 124a, the input shaft 124b, the output shaft 124c, and the movable joint shaft 124d has a through hole formed on a center axis thereof (i.e., the rotation axis of the shaft 126) so as to enable the shaft 126 to be inserted therethrough. Bearings 124e and 124f are provided in the through hole of the fixed portion 124a and the through hole of the output shaft 124c, respectively. The shaft 126 is rotatably supported by the fixed portion 124a and the output shaft 124c via the bearings 124e and 124f. Further, an inner circumferential surface of the input shaft 124b is fixed to an outer circumferential surface of the shaft 126, so as to enable the input shaft 124b to rotate integrally with the shaft 126 relative to the fixed portion 124a. In addition, the fixed portion 124a includes a solenoid (not shown) embedded therein. A surface of the movable joint shaft 124d that faces the output shaft 124c has a recessed portion formed to accommodate an input end (a left end in FIG. 2) of the output shaft 124c. Further, an outer circumferential surface of the input end of the output shaft 124c and an inner circumferential surface of the recessed portion of the movable joint shaft 124d have engagement teeth extending along a direction parallel to the rotation axis. Thereby, the movable joint shaft 124d is allowed to slide in the direction parallel to the rotation axis (the left-to-right direction in FIG. 2) along splines on the outer circumferential surface of the input end of the output shaft 124c. Further, the engagement teeth of the movable joint shaft 124d always engage with the engagement teeth of the output shaft 124c. Therefore, when the movable joint shaft 124d rotates, the output shaft 124c rotates along with the movable joint shaft 124d. Further, the movable joint shaft 124d is made of magnetic material. Therefore, when the solenoid of the fixed portion 124a is excited, the movable joint shaft 124d is attracted toward the fixed portion 124a by a magnetic attractive force, and comes into close contact with the input shaft 124b. Mutually-facing surfaces of the input shaft 124b and the movable joint shaft 124d have engagement teeth (clutch surfaces) formed to radially extend, respectively. When the movable joint shaft 124d comes into close contact with the input shaft 124b, the engagement teeth (the clutch surfaces) of the input shaft 124b and the movable joint shaft 124d come into engagement with each other, and the movable joint shaft 124d and the output shaft 124c rotate integrally with the input shaft 124b (namely, the clutch 124 is engaged). Further, the movable joint shaft 124d is urged toward the fixed portion 124a by a coil spring (not shown). Therefore, when the solenoid is degaussed, the movable joint shaft 124d is set apart from the input shaft 124b, and disengaged with the engagement teeth of the input shaft 124b, such that a driving force from the input shaft 124b is not transmitted to the movable joint shaft 124d or the output shaft 124c (namely, the clutch 124 is disengaged). Further, the output shaft 124c is connected with an input gear 125a of the second reduction gear 125. When the clutch 124 is engaged, the driving force from the input shaft 124b is transmitted to the input gear 125a of the second reduction gear 125 via the movable joint shaft 124d and the output shaft 124c. In the first mode, the clutch 124 is disengaged such that the driving force from the input shaft 124b is not transmitted to the second reduction gear 125.

Further, in the first mode shown in FIG. 2, the chuck 121 is clamped (fixed) to a distal end portion of the shaft 126 via bolts B1. Therefore, in the first mode, the chuck 121 rotates integrally with the shaft 126. Thus, in the first mode, the rotation of the output shaft of the servo motor 122 is decelerated only by the first reduction gear 123, and then transmitted to the chuck 121. A distal end (an output end) of the shaft 126 slightly protrudes from a distal end surface (a right end in FIG. 2) of an output shaft 125c of the second reduction gear 125. Hence, when the chuck 121 is clamped to the distal end portion of the shaft 126, the chuck 121 does not interfere with the output shaft 125c of the second reduction gear 125.

Figure 3:
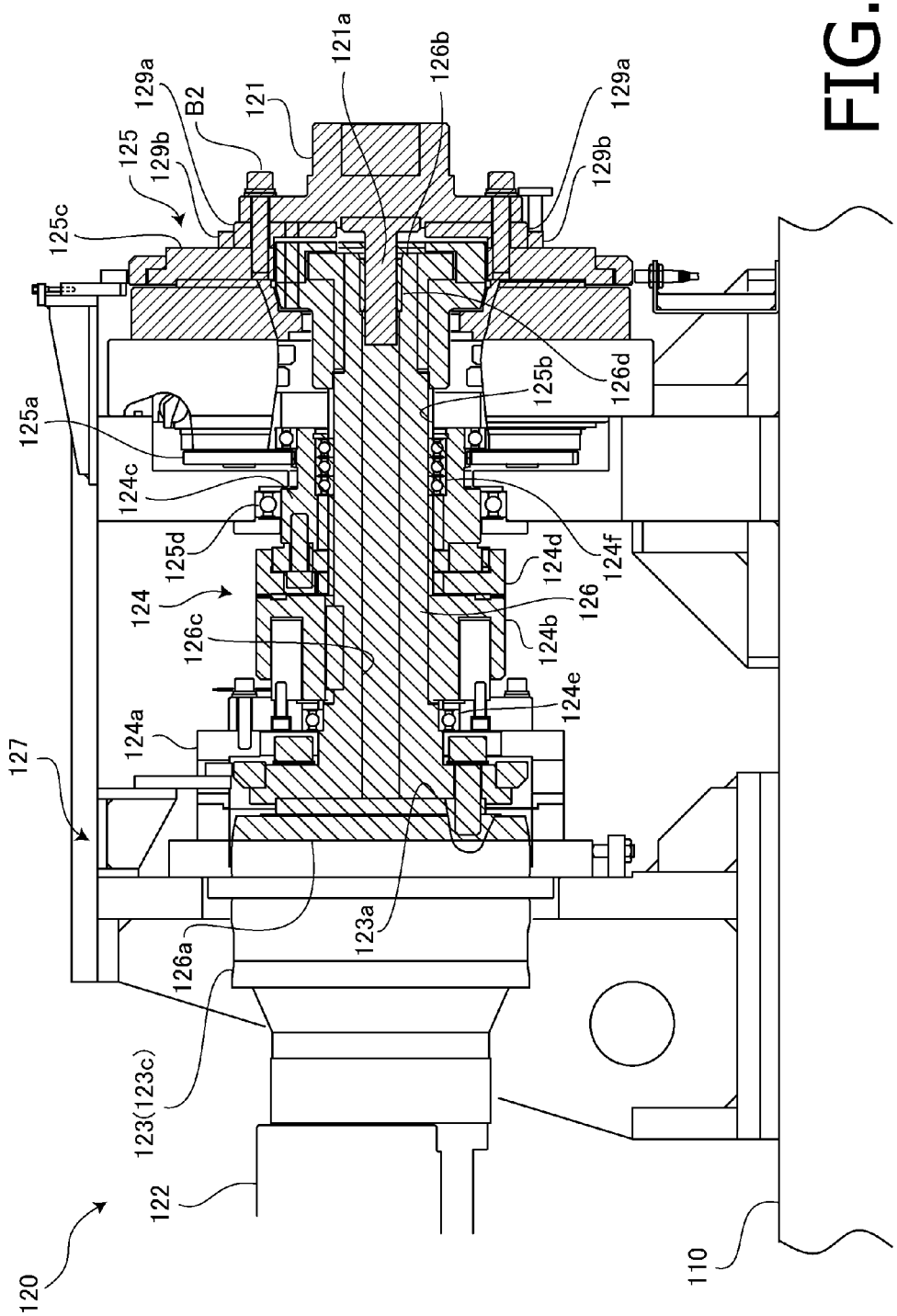
FIG. 3 is a cross-sectional side view showing the drive unit of the torsion tester in a second mode in the embodiment according to one or more aspects of the present invention.

Subsequently, the second mode will be described. FIG. 3 is a cross-sectional side view showing the drive unit 120 in the second mode. In addition, FIG. 4 is a front view of the drive unit 120 from a side of the chuck 121.

In the second mode, the respective clutch surfaces of the input shaft 124b and the movable joint shaft 124d of the clutch 124 are engaged with each other, such that the driving force from the input shaft 124b is transmitted to the output shaft 124c via the movable joint shaft 124d. It is noted that the output shaft 124c of the clutch 124 is rotatably supported by bearings 125d provided to the second reduction gear 125. Further, the bolts B1 (see FIG. 2) are detached, and the shaft 126 is disconnected from the chuck 121. Further, the chuck 121 is clamped (fixed) to the output end (output shaft) 125c of the second reduction gear 125 via bolts B2. As described above, the output shaft 124c of the clutch 124 is connected with the input gear 125a of the second reduction gear 125. Therefore, in the second mode, the driving force from the servo motor 122 is transmitted to the chuck 121 via the first reduction gear 123 and the second reduction gear 125. Namely, in the second mode, the rotation of the output shaft of the servo motor 122 is decelerated doubly by the first reduction gear 123 and the second reduction gear 125. Hence, in the second mode, the chuck 121 is driven to rotate at a higher reduction ratio (i.e., by a higher torque) in comparison with the second mode.

It is noted that, in the second mode, the shaft 126 is driven to rotate (at a higher rotational frequency than a rotational frequency of the chuck 121). Further, the output end (the distal end) of the shaft 126 protrudes from the distal end surface of the output shaft 125c of the second reduction gear 125. Therefore, in order to prevent the chuck 121 from contacting the output end of the shaft 126 or causing friction therebetween, the chuck 121 is fixed to the output end 125c of the second reduction gear 125 in a state pulled out (rightward in FIG. 3) from the position of the chuck 121 in the first mode. Further, in the second mode, there are spacer plates 129a sandwiched between the chuck 121 and the output end 125c of the second reduction gear 125, so as to maintain the state of the chuck 121 pulled out (rightward in FIG. 3).

Figure 4:
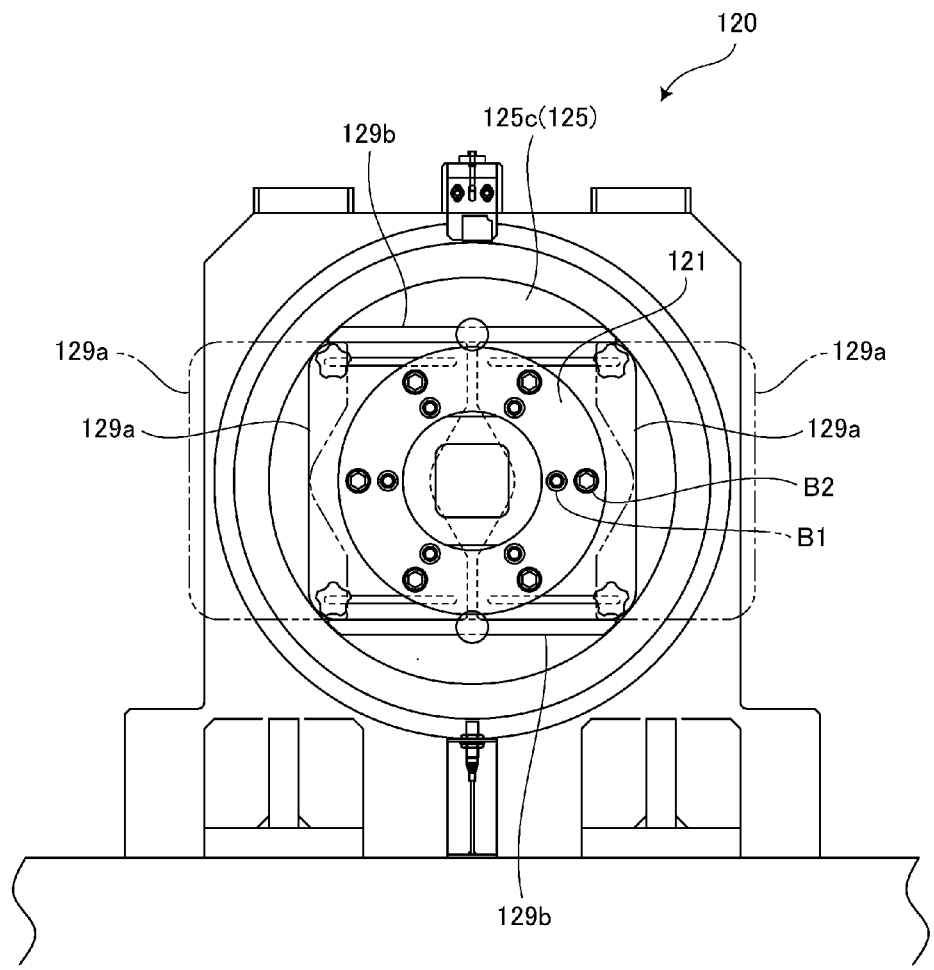
FIG. 4 is a front view of the drive unit of the torsion tester in the embodiment according to one or more aspects of the present invention.

As shown in FIG. 4, the spacer plates 129a are held to be slidable along guiderails 129b (i.e., along a direction perpendicular to a torsion axis of the torsion tester 100), in a state sandwiched between the two guiderails 129b fixed to the output end 125c of the second reduction gear 125. The spacer plates 129a are two plates disposed to interpose a rotation center of the chuck 121. In the first mode, the two spacer plates 129a are moved in such directions as to become farther away from the chuck 121 (as shown by two-dot chain lines in FIG. 4), so as to avoid interference with the chuck 121.

In order to switch from the first mode (see FIG. 2) to the second mode (see FIG. 3), the clutch 124 is engaged such that the shaft 126 is connected with the second reduction gear 125. Further, the bolts B1 are removed, and the chuck 121 is pulled out (rightward in FIG. 3). Further, the two spacer plates 129a are moved to slide closer to each other. Further, the chuck 121 is clamped (fixed), by the bolts B2, to the output end 125c of the second reduction gear 125 via the spacer plates 129a. Meanwhile, in order to switch from the second mode to the first mode, the clutch 124 is disengaged such that the shaft 126 is disconnected from the second reduction gear 125. Further, the bolts B2 are removed, and the two spacer plates 129a are moved to slide farther away from each other, to outer sides of the chuck 121. Further, the chuck 121 is pushed back (leftward in FIGS. 2 and 3), and thereafter clamped to the shaft 126 via the bolts B1.

As described above, in the embodiment, in order to switch between the first mode and the second mode, the chuck 121 is moved along the direction parallel to the rotation axis. As shown in FIGS. 2 and 3, on a surface of the chuck 121 that faces the shaft 126, provided is a shaft portion 121a extending on and along the rotation axis. The shaft portion 121a is formed with a diameter slightly smaller than the through hole 126c of the shaft 126, and is accommodated in the through hole 126c. Further, in a portion of the through hole 126c, into which the shaft portion 121a is inserted, around the distal end of the shaft 126, an oil-less bush 126d is embedded that is configured to support the shaft portion 121a in a manner rotatable around and slidable along the rotation axis. In any of the first and second modes, the shaft portion 121a of the chuck 121 is inserted into the through hole 126c. Therefore, even though the chuck 21 is moved along the direction parallel to the rotation axis so as to switch between the first mode and the second mode, the chuck 121 does not fall off.

The torsion tester 100 of the embodiment is configured such that a distance between the chucks 121 and 131 is adjusted by moving the reaction force unit 130 in an axial direction (the left-to-right direction in FIG. 1), so as to meet torsion tests (endurance tests and torsional destructive tests) for various test bodies with respective different sizes.

Figure 5:
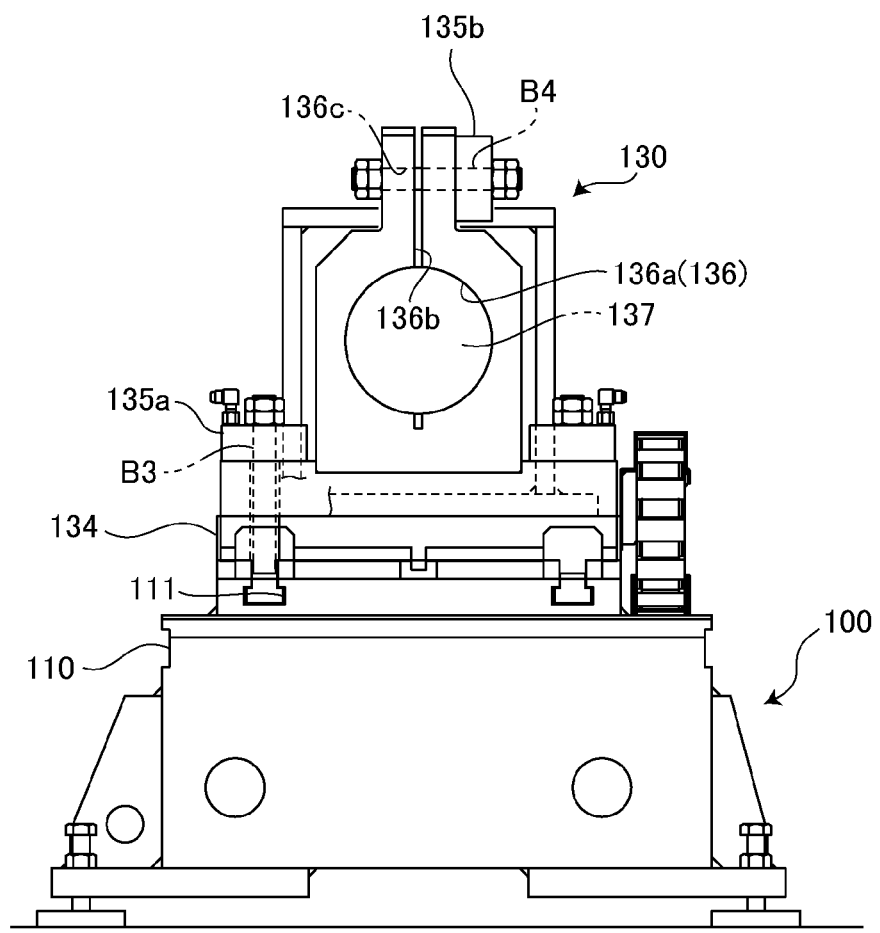
FIG. 5 is a rear view of a reaction force unit of the torsion tester in the embodiment according to one or more aspects of the present invention.

FIG. 5 is a rear view of the reaction force unit 130 (from the right side in FIG. 1). As shown in FIG. 5, two grooves 111 are formed on the base 110. The reaction force unit 130 is fixed to the base 110 using the grooves 111 and bolts B3.

Figure 6:
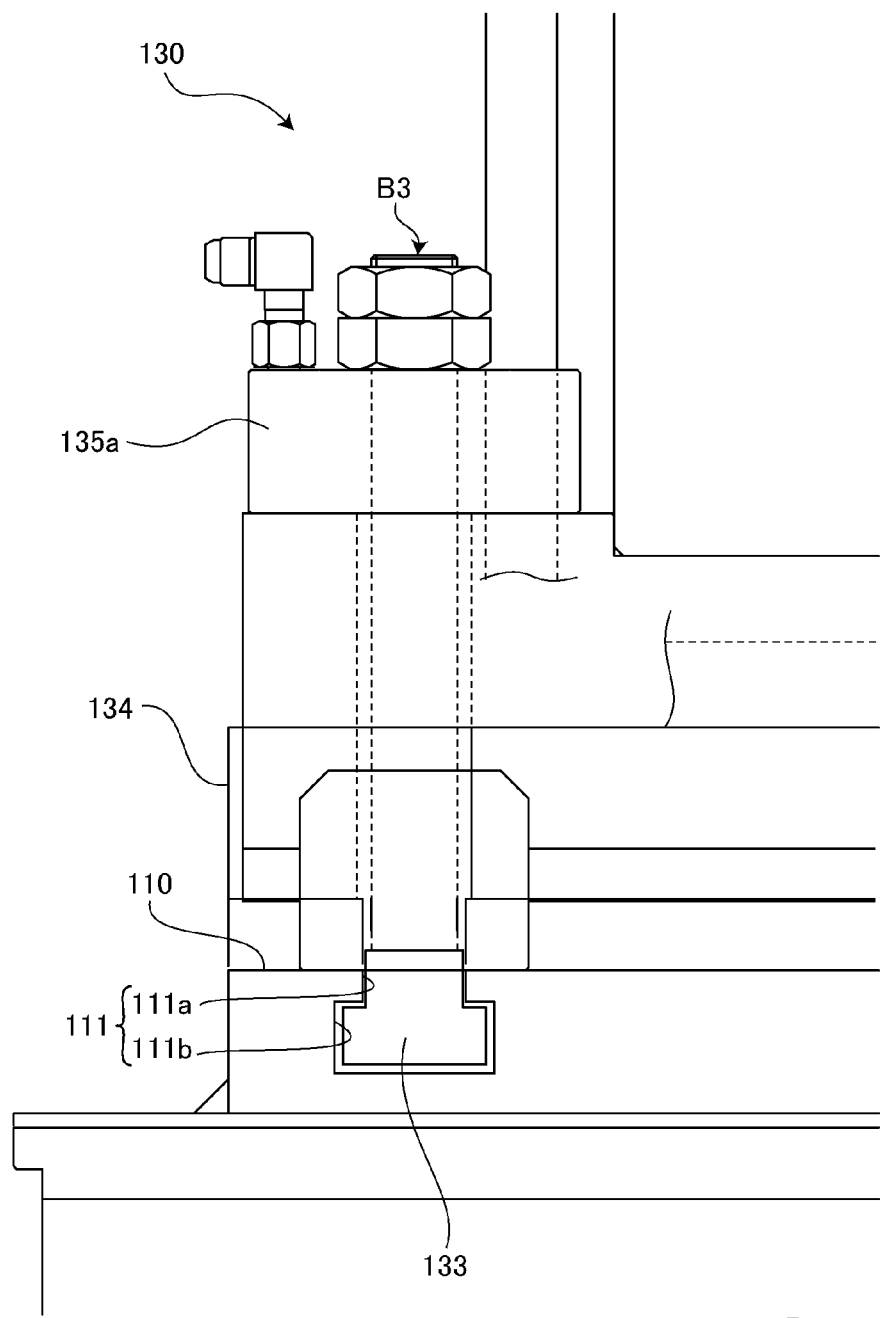
FIG. 6 is an enlarged view showing a part of the reaction force unit of the torsion tester in the embodiment according to one or more aspects of the present invention.

Hereinafter, a detailed explanation will be provided about a mechanism for fixing the reaction force unit 130 using the bolts 133. FIG. 6 is an enlarged view showing a part of the reaction force unit 130 around one of the bolts B3 shown in FIG. 5. As shown in FIG. 6, each groove 111 is a stepped groove, which is formed with an inverted T shaped cross-section such that a lower portion 111b of the groove 111 is wider than an upper portion 111a of the groove 111. Further, the bolt B3 is screwed into a nut 133 disposed at the lower portion 111b of the groove 111 and into a hydraulic nut 135a disposed on a bottom plate 134 of the reaction force unit 130. A width of the nut 133 is slightly less than a width of the lower portion 111b of the groove 111, and more than a width of the upper portion 111a. Hence, when the bolt B3 is fastened by the hydraulic nut 135a an a state where the bolt 133 is screwed into the nut 133, the bottom plate 134 and the upper portion 111a of the groove 111 are clenched between the hydraulic nut 135a and the nut 133. Consequently, the reaction force unit 130 is tightly fixed to the base 110. Meanwhile, when the bolt B3 is loosened using the hydraulic nut 135a, the clenching force applied to the bottom plate 134 and the base 110 is loosened, and the reaction force unit 130 is allowed to move along the grooves 111 in the axial direction.

The hydraulic nut 135a is configured to fasten and loosen the bolt 133 by oil pressure of externally-supplied hydraulic oil. Therefore, when moving and fixing the reaction force unit 130, an operator has only to change the oil pressure of the hydraulic oil without having to manually loosen the nut 135a.

Hereinafter, a moving mechanism of the reaction force unit 130 will be described. On the base 110, a chain 138a is disposed to be parallel to the grooves 111. Both ends of the chain 138a are fixed to the base 110. A sprocket 138b, which is configured to engage with the chain 138a, is attached to the reaction force unit 130. By rotating the sprocket 138b using a handle (not shown) in a state where the hydraulic nut 135a is loosened such that the reaction force unit 130 is allowed to move, it is possible to move the reaction force unit 130 along the chain 138a.

Further, as shown in FIG. 1, the chuck 131 and the torque sensor 132 of the reaction force unit 130 are configured to be fixed to a reaction force plate 136 fixed upright onto the bottom plate 134, via a fixed shaft 137 that is fixedly attached to the torque sensor 134. As shown in FIG. 5, the reaction force plate 136 includes a round hole 136a and a slit 136b formed to radially extend outward from the round hole 136a. Additionally, the reaction force plate 136 includes a bolt hole 136c formed to intersect the slit 136b. A diameter of the round hole 136a is slightly larger than a diameter of the fixed shaft 137. Therefore, when a bolt B4 is inserted into and through the bolt hole 136c, and is tightened by a hydraulic nut 135b, a width of the slit 136*b* is narrowed to reduce the diameter of the round hole 136*a*, and the fixed shaft 137 is clamped and fixed in the round hole 136*a*.

As described above, in the same manner as the mechanism for fixing the reaction force unit 130, the fixed shaft 137 is clamped using the hydraulic nut 135*b*. Therefore, it is possible to easily and quickly perform operations such as replacing the torque sensor 132 and/or the chuck 131, for instance, depending on specifications of the test body and/or test conditions, without having to manually tighten or loosen bolts.

Further, as shown in FIG. 1, a noncontact temperature sensor 141 is disposed above a middle position between the drive unit 120 and the reaction force unit 130. The temperature sensor 141 is held by the driver-side frame 127 via an arm 142 extending substantially in parallel with the axial direction of the torsion test (the left-to-right direction in FIG. 1). The temperature sensor 141 is configured to move along the arm 142 in the axial direction, and measure a temperature of a desired position of the test body.

Hereinabove, the embodiment according to aspects of the present invention has been described. The present invention can be practiced by employing conventional materials, methodology and equipment. Accordingly, the details of such materials, equipment and methodology are not set forth herein in detail. In the previous descriptions, numerous specific details are set forth (such as specific materials, structures, chemicals, processes, etc.) in order to provide a thorough understanding of the present invention. However, it should be recognized that the present invention can be practiced without reapportioning to the details specifically set forth. In other instances, well known processing structures have not been described in detail, in order not to unnecessarily obscure the present invention.

Only an exemplary embodiment of the present invention and but a few examples of their versatility are shown and described in the present disclosure. It is to be understood that the present invention is capable of use in various other combinations and environments and is capable of changes or modifications within the scope of the inventive concept as expressed herein. For example, the following modifications are possible. It is noted that, in the following modifications, explanations of the same configurations as exemplified in the aforementioned embodiments will be omitted.

What is claimed is:

1. A torsion tester comprising:
    a reaction force unit configured to clamp one end of a test body; and
    a drive unit configured to rotatably support and drive another end of the test body, the drive unit comprising:
        a servo motor;
        a first reduction gear configured to decelerate rotation of the servo motor at a first reduction ratio;
        a shaft configured to transmit an output force from the first reduction gear;
        a clutch having an input shaft fixed to the shaft;
        a second reduction gear configured to decelerate rotation of an output shaft of the clutch at a second reduction ratio;
        a chuck rotatably supported; and
        a connection mechanism configured to connect the chuck switchably with one of the shaft and an output shaft of the second reduction gear, and
    wherein the drive unit is configured to switch between:
        a first mode where the clutch is disengaged to interrupt power transmission between the input shaft of the clutch and the output shaft of the clutch, and the shaft is connected with the chuck by the connection mechanism; and
        a second mode where the clutch is engaged to establish the power transmission between the input shaft of the clutch and the output shaft of the clutch, and the output shaft of the second reduction gear is connected with the chuck by the connection mechanism.

2. The torsion tester according to claim 1,
wherein the clutch and the second reduction gear comprise respective hollow portions formed on and along a rotation axis of the shaft, the shaft inserted through the hollow portions.

3. The torsion tester according to claim 1,
wherein the connection mechanism comprises a slide mechanism configured to support the chuck in a manner rotatable around and slidable along the rotation axis, between:
    a first position here the chuck is in contact with a distal end portion of the shift; and
    a second position where the chuck is set apart from the distal end portion of the shaft, and
wherein the drive unit is configured to:
    operate in the first mode, when the chuck is placed in the first position, and is fixed to the distal end portion of the shaft; and
    operate in the second mode, when the chuck is placed in the second position, and is fixed to the output shaft of the second reduction gear.

4. The torsion tester according to claim 3,
wherein the slide mechanism comprises:
    a shaft portion having an end fixed to the chuck; and
    a bearing disposed at the distal end portion of the shaft, the bearing configured to support the shaft portion in a rotatable and slidable manner.

5. The torsion tester according to claim 3,
wherein the drive unit further comprises a spacer configured to maintain a distance between the chuck and the distal end portion of the shah when the chuck is placed in the second position, and
wherein the chuck is configured to, when placed in the second position, be fixed to the output shaft of the second reduction gear via the spacer that is sandwiched between the chuck and the output shaft of the second reduction gear.

6. The torsion tester according to claim 5,
wherein the drive unit further comprises a spacer supporter configured to support the spacer to he movable between:
    an effectively-set position where at least a part of the spacer is disposed between the chuck and the output shaft of the second reduction gear; and
    a withdrawal position where the spacer is withdrawn from between the chuck and the output shaft of the second reduction gear.

7. The torsion tester according to claim 2,
wherein the clutch comprises a fixed portion supported by a frame,
wherein the fixed portion, the input shaft, and the output shaft of the clutch are arranged in an order of the fixed portion, the input shaft, and the output shaft along the rotation axis,
wherein the fixed portion and the output shaft of the clutch comprise respective bearings configured to rotatably support the shaft,
wherein the second reduction gear comprises at least two bearings configured to rotatably support the output shaft of the clutch, and wherein the bearing of the output shaft of the clutch is disposed between the at least two bearings of the second reduction gear.

8. The torsion tester according to claim 1,
wherein the first mode comprises a fatigue test mode to repeatedly apply a load to the test body, and
wherein the second mode comprises a destructive test mode to apply a breaking load to the test body.

9. A torsion tester comprising:
a reaction force unit configured to clamp one end of a test body; and
a drive unit configured to rotatably support and drive another end of the test body, the drive unit comprising:
   a servo motor;
   a first reduction gear configured to decelerate rotation of the servo motor at a first reduction ratio;
   a shaft configured to transmit an output force from the first reduction gear;
   a clutch comprising;
      an input shaft fixed to the shaft and configured to he driven by the rotation decelerated by the first reduction gear via the shaft;
      an output shaft; and
      a joint mechanism engaged with the output shaft of the clutch, the joint mechanism configured to switch between a first-mode state where the joint mechanism is disengaged from the input shaft of the clutch and a second-mode state where the joint mechanism is engaged with the input shaft of the clutch;
   a second reduction gear configured to decelerate rotation of the output shaft of the clutch at a second reduction ratio;
   a chuck configured to connect switchably with one of the shaft and an output shaft of the second reduction gear, and is driven by rotation of the one of the shaft and the output shaft of the second reduction gear,
wherein the drive unit is configured to switch between:
   a first mode where the joint mechanism is set in the first-mode state such that the clutch is disengaged to interrupt power transmission between the input shaft of the clutch and the output shaft of the clutch, and the chuck is connected with the shall without involving the second reduction gear; and
   a second mode where the joint mechanism is set in the second-mode state such that the clutch is engaged to establish the power transmission between the input shaft of the clutch and the output shaft of the clutch via the joint mechanism, and the chuck is connected with the output shaft of the second reduction gear.

\* \* \* \* \*